United States Patent
Noda

(10) Patent No.: US 9,820,713 B2
(45) Date of Patent: Nov. 21, 2017

(54) IMAGE PROCESSING APPARATUS, RADIATION IMAGING SYSTEM, CONTROL METHOD, AND STORAGE MEDIUM

(71) Applicant: CANON KABUSHIKI KAISHA, Tokyo (JP)

(72) Inventor: Takeshi Noda, Ebina (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 150 days.

(21) Appl. No.: 14/941,773

(22) Filed: Nov. 16, 2015

(65) Prior Publication Data

US 2016/0151035 A1 Jun. 2, 2016

(30) Foreign Application Priority Data

Dec. 1, 2014 (JP) ................. 2014-243375

(51) Int. Cl.
*G06K 9/00* (2006.01)
*A61B 6/00* (2006.01)
*A61B 6/02* (2006.01)
*A61B 6/03* (2006.01)
*G06T 11/00* (2006.01)

(52) U.S. Cl.
CPC ............ *A61B 6/5258* (2013.01); *A61B 6/025* (2013.01); *A61B 6/032* (2013.01); *A61B 6/4233* (2013.01); *A61B 6/5205* (2013.01); *A61B 6/5235* (2013.01); *A61B 6/585* (2013.01); *G06T 11/006* (2013.01); *G06T 2211/424* (2013.01); *G06T 2211/436* (2013.01)

(58) Field of Classification Search
CPC ....... A61B 6/5258; A61B 6/025; A61B 6/032; A61B 6/4233; A61B 6/5205; A61B 6/5235; A61B 6/585; G06T 11/006; G06T 2211/424; G06T 2211/436
See application file for complete search history.

(56) References Cited

U.S. PATENT DOCUMENTS

| 6,115,445 A | * | 9/2000 | Lai .................... A61B 6/032 378/4 |
| 8,005,286 B2 | | 8/2011 | Grasruck et al. ............. 382/131 |
| 8,355,594 B2 | | 1/2013 | Noda ............................ 382/260 |

(Continued)

OTHER PUBLICATIONS

Arnold, James B., et al. "Qualitative and quantitative evaluation of six algorithms for correcting intensity nonuniformity effects." NeuroImage 13.5 (2001): 931-943.*

*Primary Examiner* — Shefali Goradia
(74) *Attorney, Agent, or Firm* — Fitzpatrick, Cella, Harper & Scinto

(57) ABSTRACT

There is provided an image processing apparatus for reconstructing a tomographic image of a subject based on a plurality of projection images obtained by detecting radiation emitted from a plurality of different positions. The image processing apparatus reconstructs a first tomographic image from the plurality of projection images, extracts a fixed pattern occurring in the first tomographic image due to a radiation detector, and forms a second tomographic image by updating the first tomographic image using a value concerning intensity of the fixed pattern as a regularization term. The image processing apparatus outputs, as the tomographic image of the subject, the second tomographic image obtained by the update.

15 Claims, 10 Drawing Sheets

(56) References Cited

U.S. PATENT DOCUMENTS

| | | | |
|---|---|---|---|
| 8,416,914 B2 | 4/2013 | Thibault et al. .................. | 378/4 |
| 8,447,078 B2 * | 5/2013 | Maschke .................. | A61B 6/14 |
| | | | 378/38 |
| 8,655,034 B2 | 2/2014 | Noda ............................ | 382/128 |
| 8,947,677 B2 * | 2/2015 | Liu ......................... | G06T 7/521 |
| | | | 356/602 |
| 2008/0056549 A1 * | 3/2008 | Hamill .................. | G06T 11/005 |
| | | | 382/131 |
| 2010/0020921 A1 * | 1/2010 | Dong .................... | A61B 6/032 |
| | | | 378/19 |
| 2010/0246759 A1 * | 9/2010 | Ogura ................... | A61B 6/025 |
| | | | 378/21 |
| 2014/0153803 A1 | 6/2014 | Noda ............................ | 382/131 |

\* cited by examiner

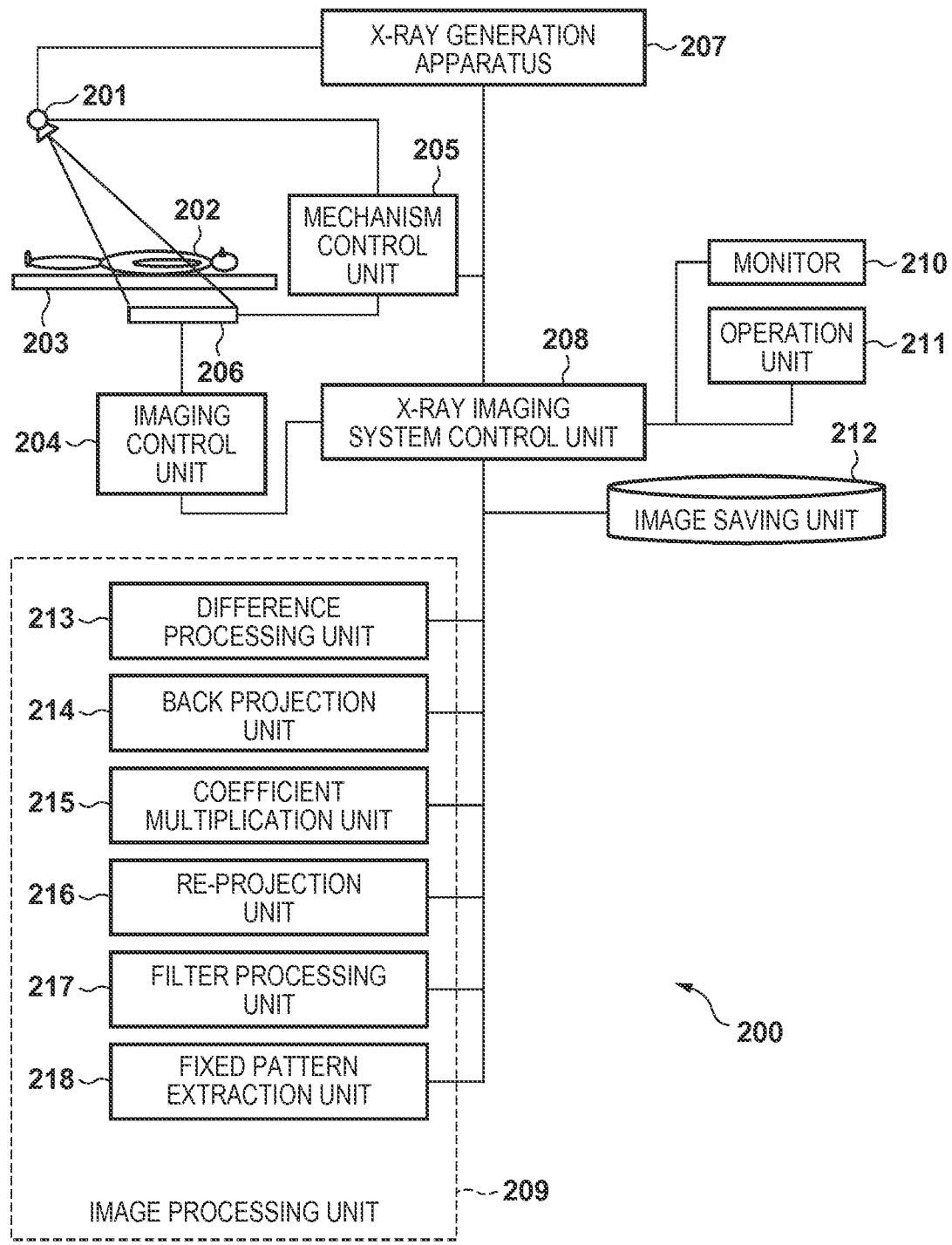

IMAGE PROCESSING APPARATUS, RADIATION IMAGING SYSTEM, CONTROL METHOD, AND STORAGE MEDIUM

BACKGROUND OF THE INVENTION

Field of the Invention

The present invention relates to image processing in tomographic image diagnosis using radiation.

Description of the Related Art

In recent years, in the radiation imaging field, tomosynthesis that detects, by a detector, radiation (X-rays) emitted at limited angles to obtain projection images, and reconstructs a tomographic image using the projection images is attracting attention. Tomosynthesis has an advantage that it can be readily applied to a fluoroscopic table, a general imaging table, a mammography apparatus, and the like without requiring a large-scale apparatus.

FIG. 1A is a schematic view showing chest imaging in a system that reconstructs a tomographic image by tomosynthesis. In tomosynthesis, projection images are captured by changing the position and irradiation angle of an X-ray tube as indicated by 101 to 103 in FIG. 1A, and also translating the position of an X-ray flat panel detector (to be referred to as an FPD hereinafter) in a direction opposite to the moving direction of the X-ray tube as indicated by 104 to 106. Note that the FPD does not move in some cases.

At this time, a point 109 at which the focal point of the X-ray tube intersects a plurality of beam axes passing through the center of the FPD is called an isocenter, and a sectional image passing through this point is clearest. Therefore, it is common practice to perform imaging by setting the isocenter 109 at the height of a portion of an object 107 to be diagnosed. However, an isocenter section 108 as a plane passing through the isocenter 109 is a plane on which a clearest tomographic image can be obtained but artifacts readily occur. The reason for this will be explained by exemplifying a shift addition method as the most basic reconstruction method of tomosynthesis.

The shift addition method is a method of obtaining a tomographic image by adding, to a sectional pixel value, the projection pixel value of a point at which a straight line connecting the focal point of the X-ray tube and a point of a section intersects the FPD. In this method, to reconstruct a point 113 on the isocenter section shown in FIG. 1B, the pixel values of points 110 to 112 on the FPD are added. Since the FPD moves as indicated by 104 to 106 along with movement of the X-ray tube indicated by 101 to 103, these points correspond to a pixel at the same position on the FPD. As a result, the tomographic pixel value of the isocenter section is obtained by adding the pixel values at the same position on the FPD at all angles (that is, by simply adding all projection images). Therefore, on the isocenter section, random noise that temporally changes is largely suppressed but fixed patterns that do not temporally change and that are caused by the FPD are emphasized.

The fixed patterns include, for example, small dirt or flaw on the surface of the FPD, the boundaries of divided driving circuits inside the FPD, the boundaries of divided substrates, and a small pattern existing in a dark image. The fixed patterns are corrected by gain correction using an X-ray image captured when no object exists, dark correction using a dark image obtained when no X-ray irradiation is performed, or the like to a level at which they do not stand out in projection images, thereby shipping the system. However, a small pattern may remain due to a difference in irradiation conditions of the X-ray tube, temporal deterioration, a change in driving load of the FPD, or the like. As a result, even if the fixed patterns do not stand out in projection images, artifacts on the isocenter section may appear at the time of reconstructing a tomographic image for the above-described reason.

Note that in tomosynthesis, a new reconstruction method such as FBP (Filtered Back Projection) or successive approximation reconstruction can be used. However, in these methods, the basic principle is the same as that of shift addition (shift addition is equivalent to CT back projection), and stronger artifacts may appear on the isocenter section due to the high-frequency emphasis effect caused by filter processing, iterative processing, or the like.

Since the isocenter section is a section on which a clearest image is obtained and which has high diagnostic value, the occurrence of artifacts degrades drawing of a lesion or organ on a tomographic image, thereby significantly reducing the diagnostic performance of the tomographic image.

Random noise is superimposed on projection images by X-ray photon noise or system noise caused by the apparatus. As a result, the tomographic image includes random noise. To cope with this, as a method of reducing random noise, U.S. Pat. Nos. 8,416,914 and 8,005,286 describe methods of reducing random noise by providing the "smoothness" of a tomographic image a priori in successive approximation reconstruction of the tomographic image. The techniques described in U.S. Pat. Nos. 8,416,914 and 8,005,286 reduce random noise by considering the energy (or its function) of the random noise at the time of successive approximation reconstruction. However, these methods do not consider the energy of fixed patterns such as the above-described artifacts on the isocenter section.

The present invention effectively reduces artifacts on an isocenter section.

SUMMARY OF THE INVENTION

According to one aspect of the present invention, there is provided an image processing apparatus for reconstructing a tomographic image of a subject based on a plurality of projection images obtained by detecting, by a detection unit, radiation emitted from a plurality of different positions, comprising: a reconstruction unit configured to reconstruct a first tomographic image from the plurality of projection images; an extraction unit configured to extract a fixed pattern occurring in the first tomographic image due to the detection unit; an update unit configured to form a second tomographic image by updating the first tomographic image using a value concerning intensity of the fixed pattern as a regularization term; and an output unit configured to output, as the tomographic image of the subject, the second tomographic image obtained by the update.

According to one aspect of the present invention, there is provided a radiation imaging system comprising: a movable emitting unit configured to emit radiation; a detection unit configured to detect the radiation; and an image processing unit configured to reconstruct a tomographic image of a subject based on a plurality of projection images obtained by detecting, by a detection unit, the radiation emitted by the emitting unit from a plurality of different positions, the image processing unit further including a reconstruction unit configured to reconstruct a first tomographic image from the plurality of projection images, an extraction unit configured to extract a fixed pattern occurring in the first tomographic image due to the detection unit, an update unit configured to form a second tomographic image by updating the first tomographic image using a value concerning intensity of the fixed pattern as a regularization term, and an output unit configured to output, as the tomographic image of the subject, the second tomographic image obtained by the update.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

FIG. 2 is a block diagram showing an example of the configuration of a radiation imaging system according to the first embodiment;

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

Although successive approximation reconstruction by an SIRT method will be exemplified below, the present invention is not limited to a successive approximation reconstruction method such as an ART method, MBIR method, or MLEM method, and the following discussion is applicable. In addition, a case in which X-rays are used as radiation will be exemplified below but other radiation may be used.

In each of the following embodiments, artifacts on an isocenter section are reduced by setting a regularization term in successive approximation reconstruction. For example, one tomographic image is back projected from a plurality of radiation images (projection images), artifacts occurring in the tomographic image are extracted, and a value concerning the extracted artifacts is included as a regularization term, thereby reducing the artifacts in the tomographic image. Then, the tomographic image is re-projected to iterate back projection of the difference between the re-projection image and the projection image, update by adding to the tomographic image, reduction of artifacts in the tomographic image by regularization, and re-projection.

Note that the artifacts are fixed patterns caused by small dirt or flaw on the surface of a flat panel detector (FPD), the boundaries of divided driving circuits inside the FPD, the boundaries of divided substrates, or the like. Note that the fixed patterns include a fixed pattern occurring as long as the FPD is used, and a temporary pattern which is caused by dirt or the like and is fixed when seen during imaging for reconstructing one tomographic image. That is, a pattern commonly occurring in captured radiation images (projection images) obtained to reconstruct one tomographic image is called a fixed pattern regardless of whether the pattern disappears in a long term.

The configuration of a radiation imaging system including an image processing apparatus for executing such processing and the procedure of image processing will be described in detail below.

First Embodiment

Figure 4A:
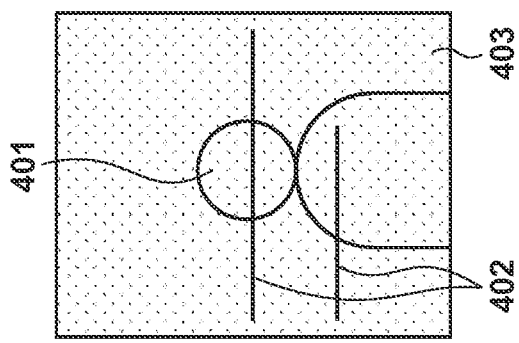
FIGS. 4A to 4C are schematic views for explaining a process of extracting artifacts each having a straight line shape.

This embodiment will explain a case in which artifacts each having a straight line shape on an isocenter section, as indicated by 402 in FIG. 4A, are reduced.

(System Configuration)

FIG. 2 shows an example of the configuration of a radiation imaging system 200 according to this embodiment. In the radiation imaging system 200, an X-ray tube 201 performs irradiation with X-rays from a plurality of projection angles. The X-ray tube 201 is movable, and can change its position and X-ray irradiation direction. A bed 203 is a table on which an object (subject) 202 is laid. An FPD (X-ray flat panel detector) 206 detects the X-rays emitted from the X-ray tube 201. The FPD 206 can be movable. A mechanism control unit 205 controls the position of the X-ray tube 201 and that of the FPD 206. For example, the mechanism control unit 205 moves the position of the X-ray tube 201 to emit the X-rays from a plurality of different positions, and causes the FPD to detect the X-rays. Furthermore, in correspondence with movement of the position of the X-ray tube 201, the mechanism control unit 205 moves the position of the FPD in a direction opposite to the direction in which the position of the X-ray tube 201 moves. An imaging control unit 204 electrically controls the FPD 206 to detect the X-rays, thereby controlling to obtain an X-ray image. An X-ray generation apparatus 207 electrically controls the X-ray tube to generate X-rays under predetermined conditions. An X-ray imaging system control unit 208 controls the mechanism control unit 205, the imaging control unit 204, and the X-ray generation apparatus 207, thereby controlling to obtain X-ray images from a plurality of X-ray irradiation positions and a plurality of angles. Note that these control processes are performed when, for example, an operation unit 211 accepts user operations.

An image processing unit 209 and an image saving unit 212 are connected to the X-ray imaging system control unit 208. The image processing unit 209 obtains a plurality of X-ray images (projection images) captured under the control of the X-ray imaging system control unit 208, and performs image processing for reconstructing a tomographic image. Note that each projection image can undergo preprocessing such as defect correction, gain correction, or logarithmic transformation before it is input to the image processing unit 209. The image saving unit 212 stores the obtained X-ray images or the reconstructed tomographic image. The X-ray imaging system control unit 208 obtains the reconstructed tomographic image from the image processing unit 209 or the image saving unit 212, and displays the result on, for example, a monitor 210.

To execute each of the above-described functions, the radiation imaging system 200 includes one or more computers. The computer includes, for example, a main control unit such as a CPU, and a storage unit such as a ROM (Read Only Memory) and a RAM (Random Access Memory). The computer may also include a graphic control unit such as a GPU (Graphics Processing Unit), a communication unit such as a network card, and an input/output unit such as a keyboard, display, or touch panel. Note that these components are connected by a bus or the like, and controlled when the main control unit executes programs stored in the storage unit.

Note that the radiation imaging system 200 may be formed as one radiation imaging apparatus or may have an arrangement including a plurality of apparatuses. For example, the radiation imaging system 200 may be a radiation imaging apparatus that integrally includes the X-ray tube 201 and the FPD 206 and includes a computer for executing the respective control processes and image processing. Furthermore, for example, the image processing unit 209 may be a computer separated from a function unit of executing radiation imaging. In this case, the image processing unit 209 is an independent image processing apparatus and, for example, obtains, via a network or storage medium, images (projection images) obtained as a result of radiation imaging, performs image processing for the obtained images, and reconstructs a tomographic image. In this case, the monitor 210 and the operation unit 211 may be connected to the image processing unit 209, or a separate monitor and operation unit may be prepared for the image processing unit 209. That is, the radiation imaging system 200 according to this embodiment may be implemented in any manner as long as a radiation detection unit (for example, an FPD) is used to detect radiation emitted from a plurality of different positions to obtain a plurality of projection images, and image processing is performed.

The image processing unit 209 reconstructs and generates a tomographic image from the obtained projection images. This processing is executed in accordance with, for example, an instruction of the X-ray imaging system control unit 208. The image processing unit 209 includes a difference processing unit 213, a back projection unit 214, a coefficient multiplication unit 215, a re-projection unit 216, a filter processing unit 217, and a fixed pattern extraction unit 218 for the image processing.

The difference processing unit 213 calculates the difference between the pixel values of corresponding pixels of two or more images. The coefficient multiplication unit 215 multiplies a value concerning artifacts by a predetermined coefficient in successive approximation reconstruction. The usage of these functions will be described in detail later.

Figure 1A:
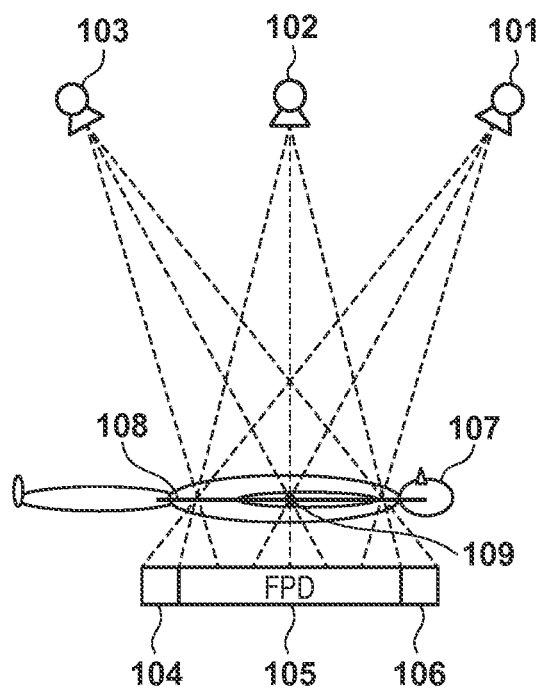
FIGS. 1A and 1B are schematic views for explaining the occurrence principle of artifacts on an isocenter section.
Figure 1B:
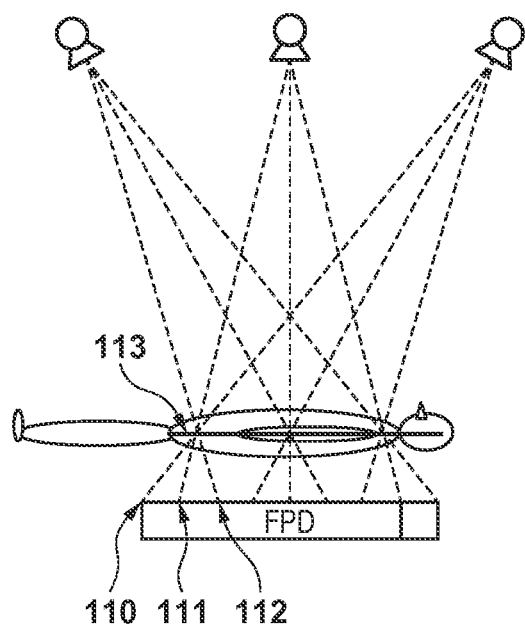
Figure 3:
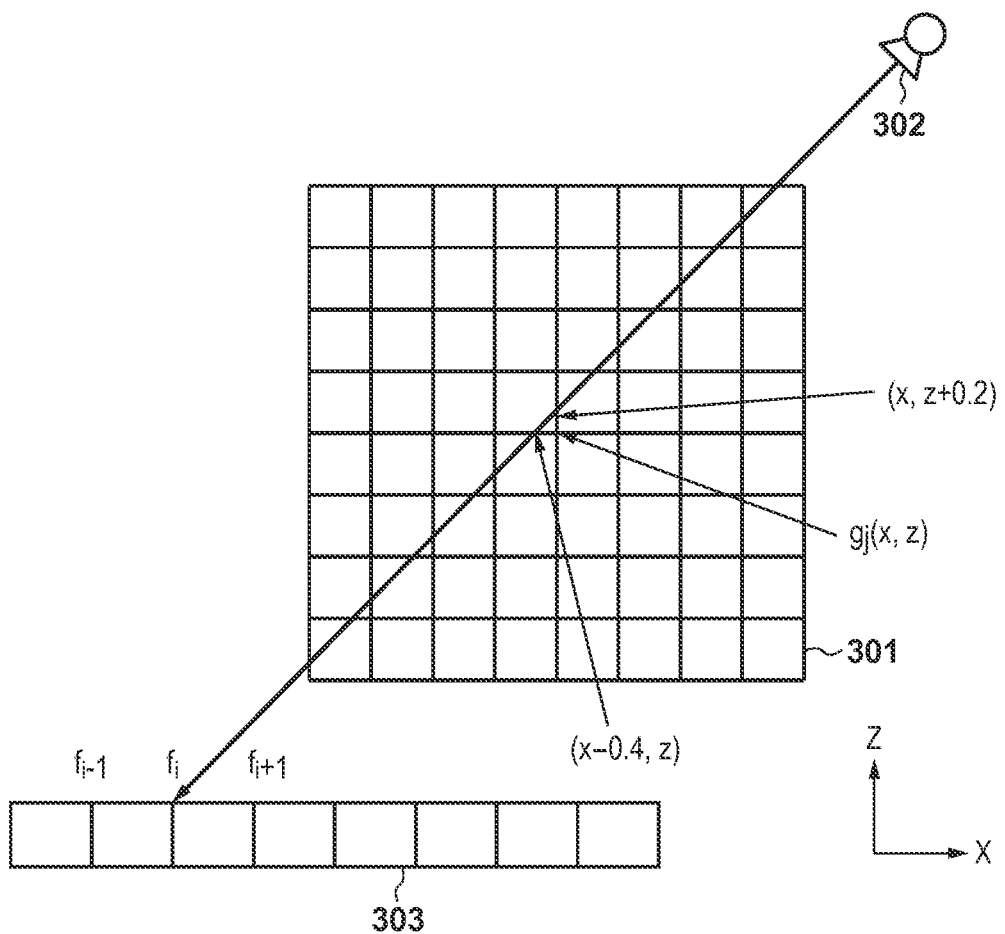
FIG. 3 is a schematic view for explaining the method of re-projection processing.

The re-projection unit 216 performs re-projection processing numerically simulating X-ray imaging. A practical method will be explained with reference to FIG. 3. Referring to FIG. 3, a grid point indicates a pixel, and a grid spacing corresponds to a pixel pitch. Note that FIG. 3 shows only an x-z plane including an x-axis in the horizontal direction and a z-axis in the vertical direction by omitting a y-axis extending in a depth direction, for the sake of simplicity. A pixel value $f_i$ of a pixel of a projection image obtained by the FPD 206 at a given projection angle is given by:

$$f_i = \sum_{j=1}^{J} C_{ij} g_j \tag{1}$$

where $g_j$ represents the pixel value of a pixel of a tomographic image 301 reconstructed from the plurality of projection images, and $C_{ij}$ represents a contribution rate of the pixel $g_j$ on the tomographic image 301 to the pixel $f_i$ on a projection image 303.

Note that i represents the ith pixel of the projection image and j represents the jth pixel of the tomographic image. In addition, J represents the total number of pixels of the tomographic image, and $C_{ij}$ represents the contribution rate of $g_j$ to $f_i$. Consider, for example, a case in which a line connecting the focal point of the X-ray tube and fi passes through (x, z+0.2) and (x−0.4, z) in the vicinity of the pixel j=(x, z). In this case, $C_{ij}$=(1.0−0.2)×(1.0−0.4)=0.48 is calculated using linear interpolation. It is only necessary to determine $C_{ij}$ as a value proportional to the contribution rate of $g_j$ to $f_i$. For example, this value may be calculated using the length crossing the pixel, bicubic or higher-order interpolation, or the area of a shape on which one pixel is projected. To simplify the description, equation (1) is represented as follows. That is, a projection image vector f including I elements $f_i$ is given by:

$$f = Cg \tag{2}$$

where C represents a projection matrix of I rows×J columns including elements $C_{ij}$, and g represents a tomographic image vector including J elements $g_j$.

Contrary to the re-projection unit 216, the back projection unit 214 performs a back projection operation of distributing the pixel values from the projection images to the tomographic image again. That is, the back projection unit 214 reconstructs the tomographic image from the projection images. This operation can be expressed by:

$$g_j = \sum_{i=1}^{I} C_{ij} f_i \tag{3}$$

where I represents the total number of pixels of the projection image. Similarly to equation (2), by using a vector and matrix, equation (3) is indicated by:

$$g = C^T f \tag{4}$$

where a back projection matrix $C^T$ is a transposed matrix of the projection matrix C.

Figure 4B:
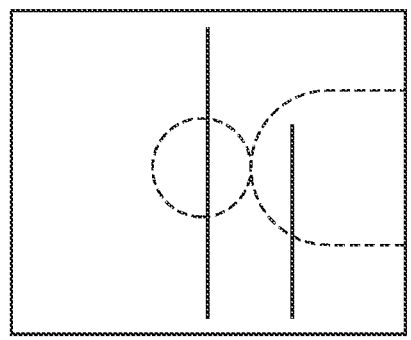

The filter processing unit 217 performs low-pass filter processing for the reconstructed tomographic image in a direction parallel to the artifacts each having a straight line shape. This reduces the influences of random noise and object on the tomographic image without changing the shapes of the artifacts, thereby readily extracting the artifacts. As shown in FIG. 4A, the tomographic image on the isocenter section includes a subject 401, the artifacts 402, and random noise 403 which are superimposed on each other. In this embodiment, since the artifacts 402 appear as fixed patterns each having a straight line shape running in the horizontal direction, low-pass filter processing is performed in the horizontal direction (x direction), thereby obtaining a pixel value $I_{out}(x, y)$ of a pixel (x, y) of the tomographic image (FIG. 4B) after the filter processing, given by:

$$I_{out}(x, y) = \sum_{i=-n}^{n} L_i I_{in}(i, y) \quad (5)$$

where $I_{in}(i, y)$ represents a pixel of the tomographic image before the filter processing. With respect to a pixel value g(x, y) at the coordinates (x, y) of the tomographic image, $I_{in}(i, y)=g(x+i, y)$. Note that x or i indicates the abscissa of the tomographic image and y indicates the ordinate of the tomographic image. Furthermore, $L_i$ represents the coefficient of a low-pass filter. For example, for an average value filter of n=4, $L_i=\frac{1}{9}$. Note that a general filter such as a Gaussian filter may be used as a low-pass filter. As described above, the low-pass filter processing can suppress random noise without degrading the artifacts as shown in FIG. 4B, thereby reducing the pixel values of the subject 401.

For the following description, by using a matrix L including elements Li, the low-pass filter processing in the filter processing unit 217 is expressed by:

$$I_{out}=LI_{in}=Lg \quad (6)$$

Figure 4C:
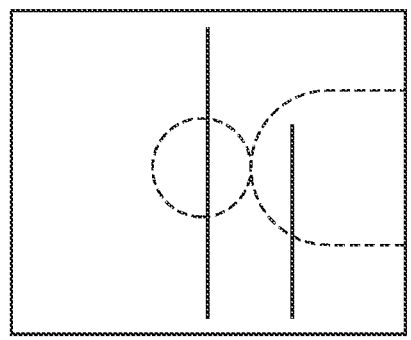
Figure 5:
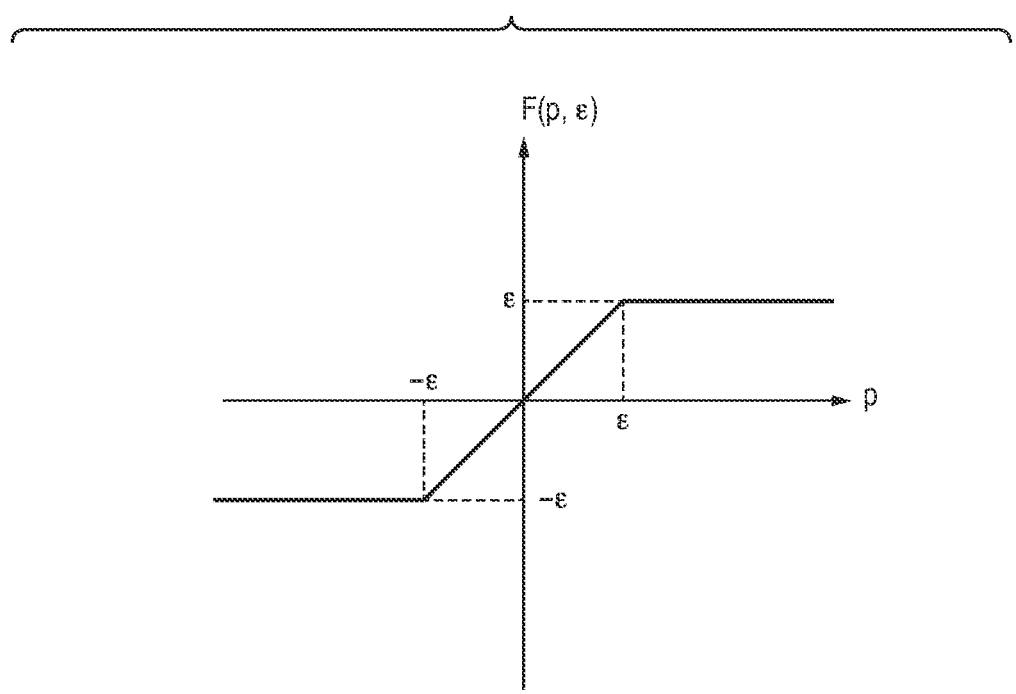
FIG. 5 is a graph showing a nonlinear function used in fixed pattern extraction processing.

The fixed pattern extraction unit 218 extracts an artifact image from the pixel value $I_{out}(x, y)$ of the tomographic image processed by the filter processing unit. This processing can be described as nonlinear processing. That is, a pixel value $J_{out}(x, y)$ of an image (FIG. 4C) after fixed pattern extraction processing is given by:

$$J_{out}(x, y) = \sum_{j=-m}^{m} V_j F(J_{in}(x, y) - J_{in}(x, j+y), \varepsilon) \quad (7)$$

where $J_{in}(x, y)$ is the pixel value $I_{out}(x, y)$ of FIG. 4B before the fixed pattern extraction processing, and $V_j$ represents the coefficient of a low-pass filter. For an average value filter of m=1, $V_j=\frac{1}{3}$. Furthermore, F represents a piecewise linear function having ±ε as division points, as shown in FIG. 5. That is, F is a function of performing nonlinear processing for limiting an output when the magnitude of the difference (contrast) between the pixel value of the pixel $J_{in}(x, y)$ to be processed and that of the surrounding pixel $J_{in}(x, j+y)$ is equal to or larger than ε. In general, the artifacts 402 on the isocenter section have only contrast smaller than that of the subject 401. Therefore, it is possible to prevent the fixed pattern extraction unit 218 from extracting the subject 401 by setting ε in correspondence with the intensity of the artifacts.

For the following description, $J_{out}$ is given by:

$$t_{out}=VJ_{in}=VI_{out}=VLg \quad (8)$$

where V indicates the processing of the fixed pattern extraction unit 218. Note that the processing V is a nonlinear function. Thus, strictly speaking, it is impossible to express $J_{out}$ by a linear matrix operation given by equation (8). However, this is used for the descriptive purpose. Note that in fact, for example, the matrix V for approximating linear processing is calculated from the obtained output $J_{out}(x, y)$, and the input $J_{in}(x, y)$, that is, $I_{out}(x, y)$.

In general, when performing successive approximation reconstruction by the least square norm, the tomographic image g is reconstructed by minimizing a square error given by:

$$s=(Cg-f)^2 \quad (9)$$

That is, in this case, the tomographic image g is updated and reconstructed so as to minimize the square error s of the re-projection image Cg of the tomographic image and the captured projection image f.

In this embodiment, $(VJ_{out})^2=(VLg)^2$ as the intensity (energy) of the artifacts is used as a regularization term in addition to the square error. That is, in this embodiment, in successive approximation reconstruction, the pixel value g of the tomographic image is updated to form a tomographic image to be finally output so as to reduce $$s=(Cg-f)^2+\alpha(VLg)^2 \quad (10)$$

where α represents a coefficient for adjusting the degree of regularization, and is used for multiplication by the coefficient multiplication unit 215. When the value of equation (10) is suppressed to a small value, the tomographic image is reconstructed and the energy of the artifacts on the isocenter section is reduced. Consequently, it is possible to prevent the fixed patterns from being strongly reflected on the reconstructed tomographic image. With this processing, it is possible to suppress the influence on the pixels of a subject portion of the tomographic image, as compared with, for example, a case in which fixed patterns are extracted and are then subtracted from the reconstructed tomographic image.

Procedure of Image Processing

Figure 6:
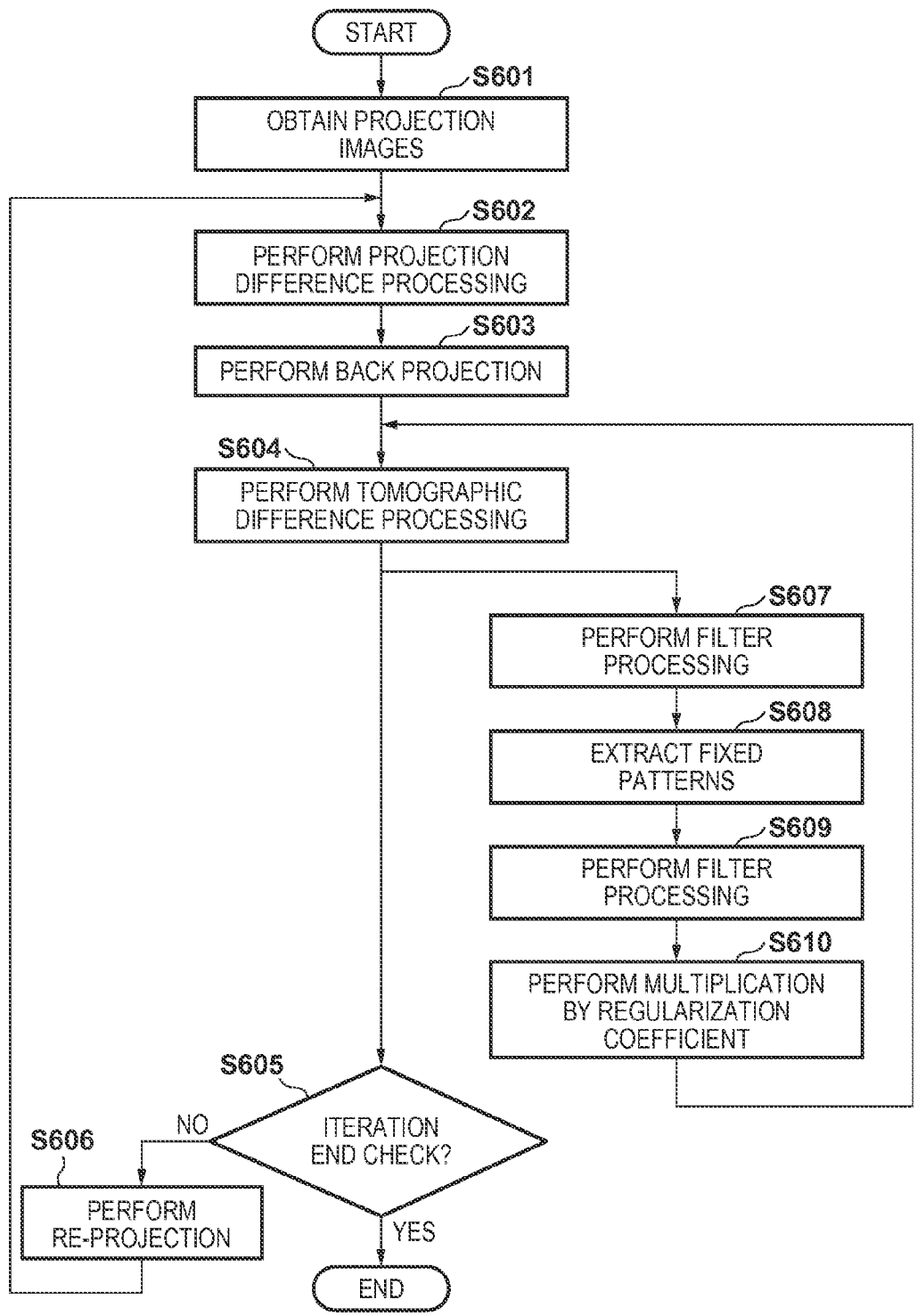
FIG. 6 is a flowchart illustrating the procedure of imaging processing according to the first embodiment.

An example of the procedure of successive approximation reconstruction processing according to this embodiment will be described with reference to FIG. 6.

In step S601, projection images are obtained. This processing is performed by capturing the object 202 with X-rays while changing the position and X-ray irradiation angle of the X-ray tube 201. The projection angle and the number of captured images depend on the performance and specifications of the apparatus. For example, if 81 projection images are captured at 15 FPS (Frames Per Second) while changing the angle from −40° to +40° by 1°, they can be collected for about 6 sec. Arbitrary values are settable as X-ray imaging conditions. For example, about 100 kV and 1 mAs can be set as imaging conditions for chest imaging or the like. In addition, the distance between the FPD 206 and the X-ray tube 201 can be set within the range from about 100 cm to 150 cm, which is the setting range of a fluorography apparatus or a general imaging apparatus.

The FPD 206 is translated in a direction opposite to the moving direction of the X-ray tube 201. A translation amount at this time is given by P×tan(β) where β represents the X-ray irradiation angle and P represents the distance between the rotation center of the X-ray tube 201 and the center of the FPD 206. By translating the FPD 206 in this way, the reference axis of the X-ray tube always passes through the center of the FPD 206 even when the position and X-ray irradiation direction of the X-ray tube 201 change.

The series of obtained projection images is preprocessed, and is then input to the image processing unit 209. The preprocessing is, for example, correction of a defect pixel and dark current of the FPD 206, correction of an irradiation error attributed to the X-ray tube 201, or logarithmic transformation. These processes can be processes which are generally executed in the FPD. With logarithmic transformation, the pixel value of the projection image is obtained as the line integral of an X-ray attenuation coefficient. The projection image is reconstructed based on the additivity of this X-ray attenuation coefficient.

Successive approximation reconstruction is performed to iteratively decrease the value of equation (10) in step S602 and subsequent steps. To minimize the value of equation (10), it is possible to obtain the pixel value g of the tomographic image by an inverse matrix operation by, for example, setting s of equation (10) to 0. However, in reconstruction of the tomographic image by this method, the matrix size becomes too large to readily store and calculate an inverse matrix. To cope with this, the pixel value g of the tomographic image that provides the minimum value or minimal value of the value of equation (10) is searched for by successively decreasing the value of equation (10) using an iterative method like a steepest decent method or conjugate gradient method. Note that a case in which the steepest decent method is used will be explained. In this case, an iterative equation is given by:

$$g^{k+1} = g^k - \frac{\partial s}{\partial g^k} = g^k - C^T(Cg^k - f) - \alpha L^T V^T V L g^k \quad (11)$$

where k represents an iterative count, and $g^k$ represents a tomographic image obtained by the kth iterative processing. Note that the term of $\partial s/\partial g^k$ may be multiplied by a coefficient smaller than 1. Note that the filter processing L and the fixed pattern extraction processing V are generally symmetric, and thus equation (11) is rewritten by:

$$g^{k+1} = g^k - C^T(Cg^k - f) - \alpha L V^2 L g^k \quad (12)$$

An iterative process of reconstructing and updating the tomographic image based on equation (12) will be described with reference to the procedure of step S602 and subsequent steps.

In step S602, the difference processing unit 213 creates a projection image residual vector $df^k$ as a difference value obtained as a result of subtracting the projection image f obtained in step S601 from a re-projection image $Cg^k$ of the tomographic image re-projected in step S606, given by:

$$df^k = cg^k - f \quad (13)$$

Note that in step S606, the re-projection unit 216 forms the re-projection image $Cg^k$ using the tomographic image $g^k$. If the processing in step S606 has not been performed, for example, at the start of the processing, the difference processing may be performed by setting $Cg^0$ to 0 or by using a non-zero initial value $Cg^0$. The projection image residual vector $df^k$ indicates the difference in pixel value between the re-projection result of the tomographic image $g^k$ in the kth iterative processing and the projection image f obtained in actual imaging.

In step S603, the back projection unit 214 back projects the difference projection image $df^k$ generated in step S602 to generate a tomographic image change vector $dg^k$ by:

$$dg^k = C^T df^k \quad (14)$$

The tomographic image change vector $dg^k$ indicates the change amount of the first term on the right-hand side of equation (10) when the value of $g^k$ changes.

Subsequently, in step S604, the difference between the tomographic image $g^k$ and the sum of the tomographic image change vector $dg^k$ and an artifact energy change vector $\alpha(z)dE^k$ obtained by performing multiplication by a coefficient $\alpha(z)$ is calculated. Then, a tomographic image $g^{k+1}$ in the (k+1)th iterative processing is obtained by:

$$g^{k+1} = g^k - dg^k - \alpha(z)dE^k = g^k - C^T(Cg^k - f) - \alpha L V^2 L g^k \quad (15)$$

A method of obtaining the artifact energy change vector $dE^k$ at this time will be described later. Note that this artifact energy change vector may initially be a zero vector.

After that, in step S605, it is determined whether to end the iterative processing. This determination processing is performed by, for example, determining whether the tomographic image change vector $dg^k$ is equal to or smaller than a predetermined value. Alternatively, the determination processing may be performed by, for example, determining whether the iterative count reaches a predetermined count or whether the difference between the obtained tomographic image $g^{k+1}$ and the tomographic image $g^k$ before the update processing is equal to or smaller than a predetermined value. For example, when the difference between the tomographic images before and after the update processing is equal to or smaller than the predetermined value or when the iterative count reaches the predetermined count, it is determined not to perform the iterative (update) processing any more. If it is determined not to end the iterative processing, the process advances to step S606, and the re-projection unit 216 re-projects $g^k$ to generate $Cg^{k+1}$, thereby iterating the procedure from step S602. If it is determined to end the iterative processing, the tomographic image $g^{k+1}$ is output as a complete tomographic image g.

On the other hand, in step S607, the filter processing unit 217 performs low-pass filter processing for the tomographic image $g^{k+1}$ obtained by equation (15) in a direction parallel to the artifacts. In step S608, the fixed pattern extraction unit 218 performs processing of extracting the artifacts (fixed patterns) from the tomographic image having undergone the filter processing in step S607. This processing is performed twice. Note that the matrix V concerning the fixed pattern extraction processing may be obtained by calculating the matrix V for approximating linear processing from an output obtained in the extraction processing and an input at this time, as described above. In this case, a tomographic image $Lg^{k+1}$ after the low-pass filter processing may be multiplied by the square of the matrix. In step S609, the filter processing unit 217 performs the low-pass filter processing for an artifact image extracted in step S608 in the direction parallel to the artifacts. With respect to the low-pass filter processing, calculation may be performed by a matrix operation.

With the processes in steps S607 to S609, the artifact energy change vector $dE^k$ is obtained by:

$$dE^k = L V^2 L g^k \quad (16)$$

This artifact energy change vector $dE^k$ indicates the change amount of the second term on the right-hand side of equation (10) when the value of $g^k$ changes.

Note that if the running direction of the artifacts is not known in advance, the above-described respective processes may be performed based on low-pass filter processes in a plurality of directions, and fixed patterns running in the respective directions may be extracted and combined, thereby extracting the overall image of the artifacts.

Figure 7:
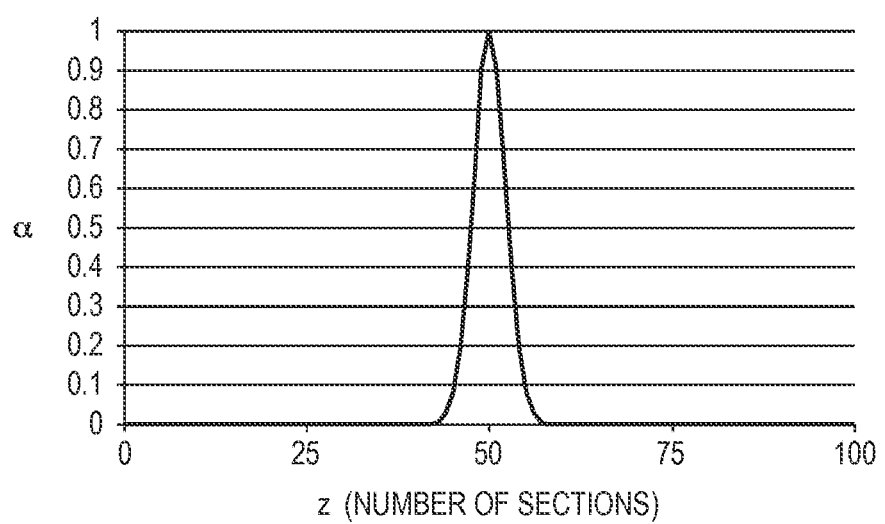
FIG. 7 is a graph showing the magnitude of a coefficient for determining the degree of regularization with respect to a section height.

After that, in step S610, the coefficient multiplication unit 215 multiplies the artifact energy change vector $dE^k$ by the coefficient $\alpha(z)$. The regularization coefficient $\alpha(z)$ is a term representing the magnitude of the energy of the artifacts, and z represents the number of sections (a section height). As described above, the artifacts on the isocenter section appear on the isocenter section most strongly but they may influence on a tomographic image near the isocenter, and abruptly decrease as the isocenter section is farther away. Consequently, by setting the coefficient $\alpha(z)$ to have a Gaussian shape shown in FIG. 7, it is possible to express the energy of the artifacts whose intensity increases as the sectional image is closer to the isocenter section. FIG. 7 shows an example in which the total number of tomographic images is 100 and the 50th image corresponds to the isocenter section. In this example, α(z) becomes largest in the 50th image (isocenter section), and abruptly decreases in a tomographic image away from the 50th image.

The artifact energy change vector $\alpha(z)dE^k$ obtained by performing multiplication by the coefficient $\alpha(z)$ is subtracted from the reconstructed tomographic image $g^k$ in step S604, as described above. Note that in step S604, the tomographic image change vector $dg^k$ is also subtracted from the pixel value $g^k$ of the reconstructed tomographic image, as described above.

In this way, the pixel value $g^k$ of the tomographic image is iteratively updated. When it is considered that the value of equation (10) becomes minimum or minimal, that is, the magnitude of the difference between the pixel value vectors before and after the update processing is equal to or smaller than a predetermined value, the pixel value vector at this time (after or before the update processing) is output as a reconstructed tomographic image of the subject.

In the successive approximation reconstruction method, a rough low-frequency structure of the subject is reconstructed at the initial stage of the iterative processing, and a finer high-frequency structure is formed as the iterative processing advances. In general, artifacts on the isocenter section often have a fine high-frequency structure. Therefore, with the method according to this embodiment, it is possible to suppress an increase in energy of the artifacts on the isocenter section in successive approximation reconstruction, and prevent the artifacts on the isocenter section from being formed in the iterative process.

As described above, according to this embodiment, it is possible to effectively suppress the occurrence of artifacts each having a straight line shape on the isocenter section. Since the isocenter section is a section on which a clearest image is obtained, it is possible to reconstruct a tomographic image with high diagnostic performance by using the above-described method, as compared with the conventional method.

Second Embodiment

In this embodiment, a case in which fixed patterns each having an indeterminate shape (curved line shape) instead of a straight line shape in the first embodiment are reduced will be described. Note that the method according to this embodiment is applicable to a case in which fixed patterns each having a straight line shape occur as in the first embodiment.

(System Configuration)

Figure 8:
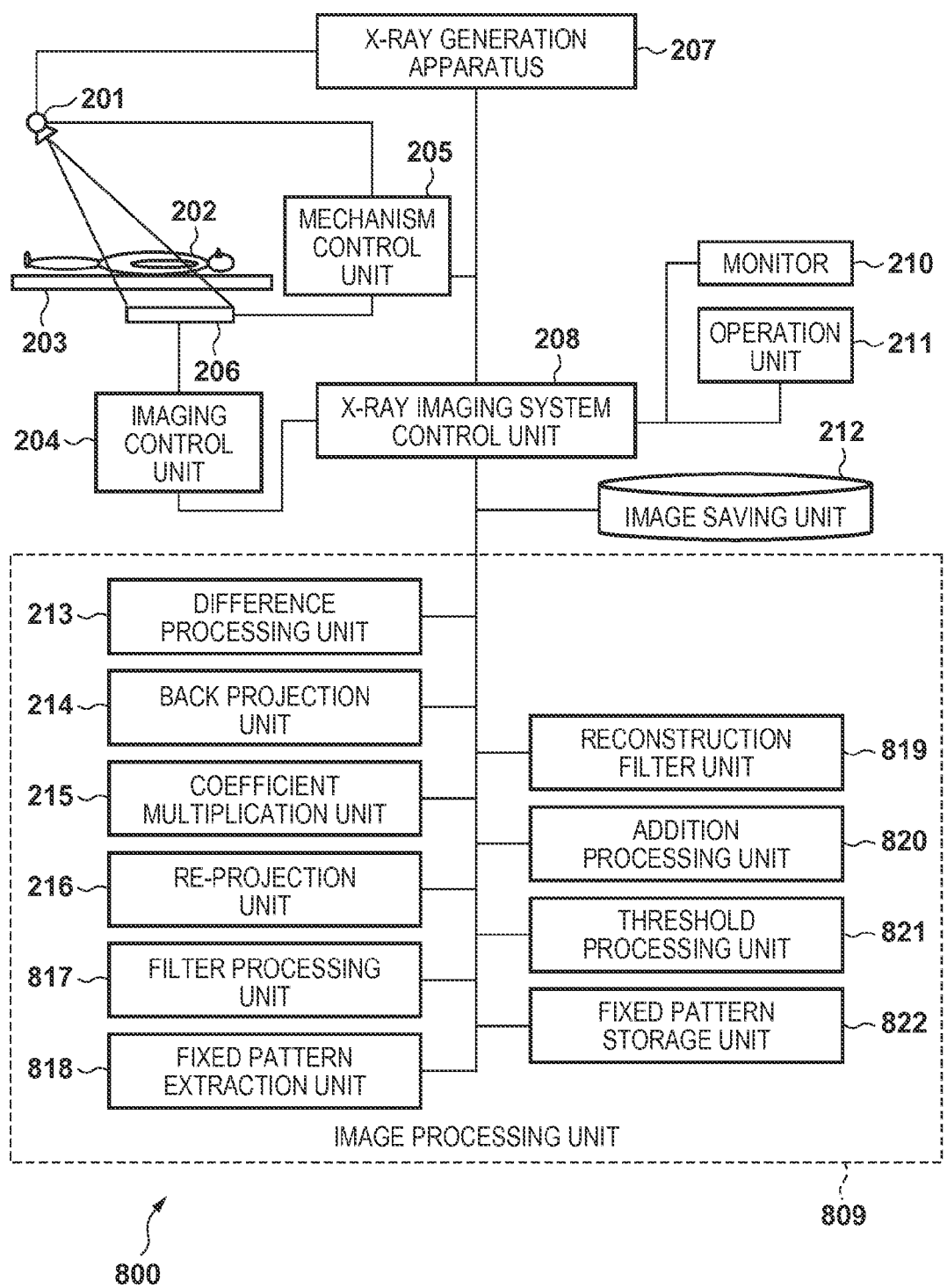
FIG. 8 is a block diagram showing an example of the configuration of a radiation imaging system according to the second embodiment.

FIG. 8 shows an example of the configuration of a radiation imaging system 800 according to this embodiment. Note that the same reference numerals as those in the first embodiment denote the same functions and a detailed description thereof will be omitted. In this embodiment, an image processing unit 809 includes a reconstruction filter unit 819, an addition processing unit 820, a threshold processing unit 821, and a fixed pattern storage unit 822. The image processing unit 809 according to this embodiment includes a filter processing unit 817 and fixed pattern extraction unit 818 which execute processes different from those executed by the filter processing unit 217 and fixed pattern extraction unit 218 in the first embodiment and can perform processes along arbitrary lines. These functions are used to extract artifact patterns each having an indeterminate shape on an isocenter section, as indicated by 901 in FIG. 9A, from each of a plurality of projection images captured by the radiation imaging system 800, and store them.

The reconstruction filter unit 819 performs reconstruction filter processing for the projection image. An output projection image $I_{out}(x, y)$ is given by:

$$I_{out}(x, y) = \sum_{j=-n}^{n} I_{in}(x, j)H_j \tag{17}$$

where $I_{in}(x, j)$ represents an input projection image, and H represents a reconstruction filter coefficient. A reconstruction filter is generally a filter used to reconstruct a tomographic image using FBP (Filtered Back Projection), for example, a RAMP filter or Shepp & Logan filter. Assume that this embodiment uses the Shepp & Logan filter expressed by:

$$H_j = \frac{2}{\pi^2(1-4j^2)} \tag{18}$$

The reconstruction filter processing is performed in a direction parallel to the moving direction of an X-ray tube 201 or an FPD 206. Since the reconstruction filter is a high-frequency emphasis filter without any DC component, this processing extracts fixed patterns each in a shape like a line drawing shown in FIG. 9B on the isocenter section.

Figure 9C:
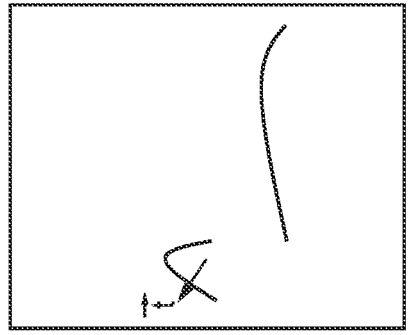
FIGS. 9A to 9C are first schematic views for explaining a process of extracting artifacts each having a curved line shape.
Figure 10C:
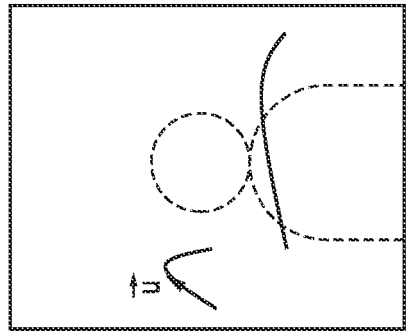
FIGS. 10A to 10C are second schematic views for explaining a process of extracting artifacts each having a curved line shape.
Figure 10B:
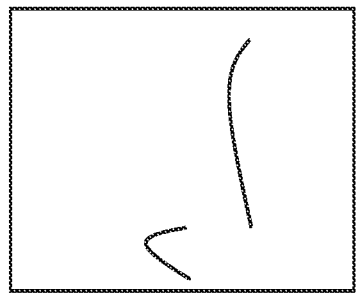
Figure 10A:
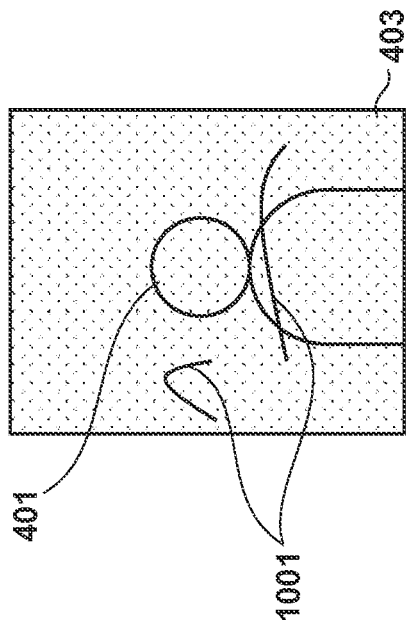

The addition processing unit 820 adds two or more projection images to generate one image shown in FIG. 9C. The threshold processing unit 821 binarizes the image using a predetermined threshold. The fixed pattern storage unit 822 stores the binarized artifact patterns (fixed patterns). The filter processing unit 817 performs low-pass filter processing along a tangential direction u of the artifact shown in FIG. 10B. A pixel $I_{out}(x, y)$ in FIG. 10B after the filter processing is given by:

$$I_{out}(x, y) = \sum_{i=-n}^{n} L_i I_{in}(x_i, y_i)\Delta u_i \tag{19}$$

where $I_{in}(x, y)$ represents a pixel in FIG. 10A before the filter processing. In addition, x and y indicate the abscissa and ordinate of the tomographic image, respectively, $\Delta u_i$ indicates a line element along the tangential line of the artifact, and $L_i$ indicates the coefficient of a low-pass filter. For example, for an average value filter of n=4, $L_i=1/9$. Note that a general filter such as a Gaussian filter may be used as a low-pass filter. This processing makes it easy to extract the artifact by reducing the influences of random noise and object without changing the shape of the artifact.

As in the first embodiment, the low-pass filter processing of the filter processing unit 817 is given by:

$$I_{out} = LI_{in} \tag{20}$$

The fixed pattern extraction unit 818 extracts an artifact image from the tomographic image processed by the filter processing unit. This processing can be described as non-linear processing in a normal direction t of the artifact shown in FIG. 10C. That is, a pixel value $J_{out}(x, y)$ in FIG. 10C after fixed pattern extraction processing is given by:

$$J_{out}(x, y) = \sum_{j=-m}^{m} V_j F(J_{in}(x, y) - J_{in}(x_j, y_j), \varepsilon) \tag{21}$$

where $J_{in}(x, y)$ is the pixel value $I_{out}(x, y)$ in FIG. 10B before the fixed pattern extraction processing. In addition, x and y indicate the abscissa and ordinate of the tomographic image, respectively, and $V_j$ indicates the coefficient of the low-pass filter. For an average value filter of m=1, $V_j=\frac{1}{3}$. Furthermore, F represents a piecewise linear function having $\pm\epsilon$ as division points, as shown in FIG. 5. That is, F represents a function of limiting an output when the magnitude of the difference between the pixel value $J_{in}(x, y)$ to be processed and a surrounding pixel value $J_{in}(x_j, y_j)$ is equal to or larger than E. In general, artifacts 1001 on the isocenter section have only contrast smaller than that of a subject 401. Therefore, it is possible to prevent the fixed pattern extraction unit 818 from extracting the subject 401 by setting $\epsilon$ to a value corresponding to the intensity of the artifacts.

As in the first embodiment, $J_{out}$ is given by:

$$J_{out}=VJ_{in} \qquad (22)$$

where V indicates the processing of the fixed pattern extraction unit 818. As in the first embodiment, as a consequence of successive approximation reconstruction according to this embodiment, by using the above notation, a pixel value g of the tomographic image is updated to form a tomographic image to be finally output so as to reduce $$s=(Cg-f)^2+\alpha(VLg)^2 \qquad (23)$$

Procedure of Image Processing

Figure 11:
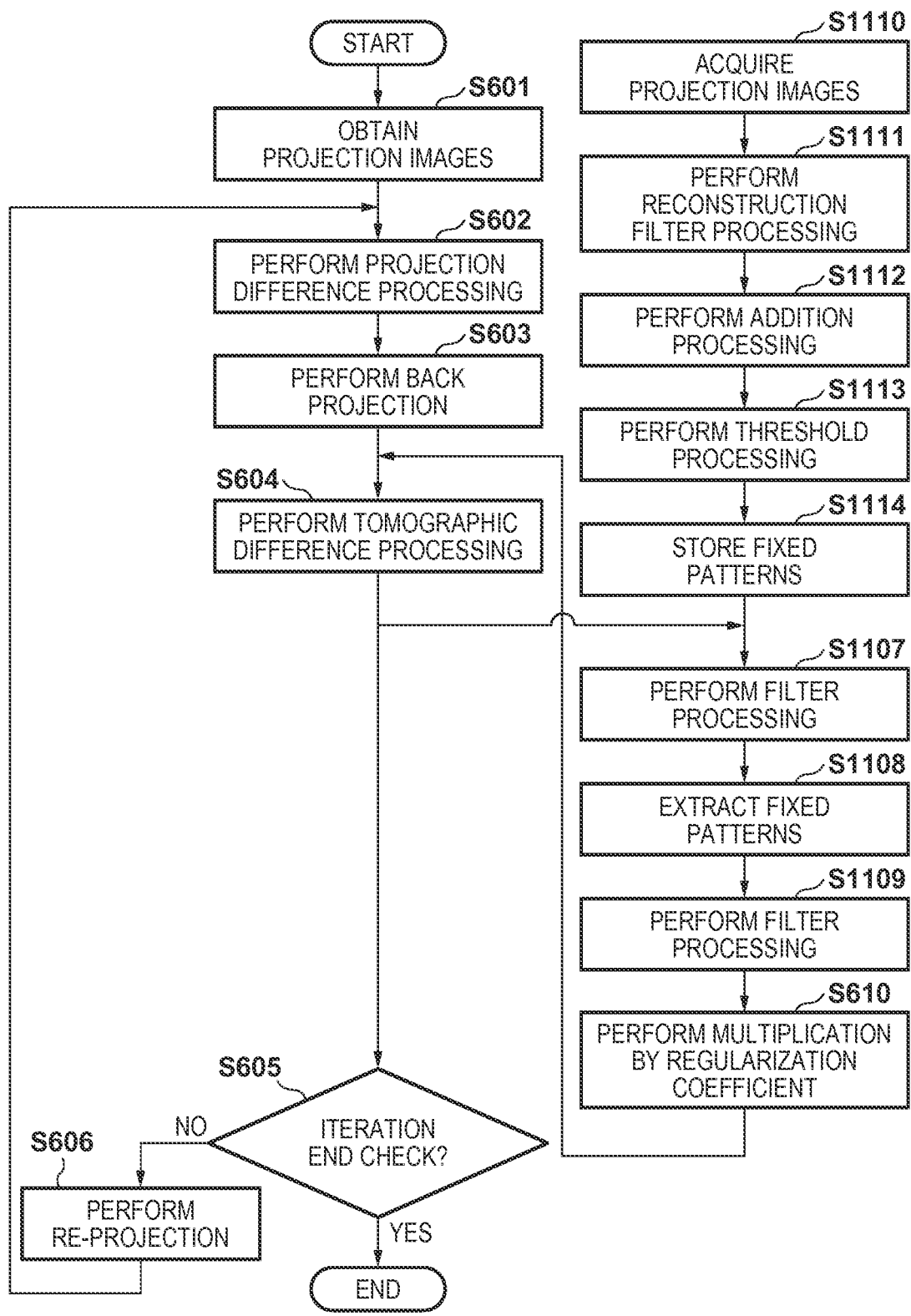
FIG. 11 is a flowchart illustrating the procedure of image processing according to the second embodiment.

An example of the procedure of successive approximation reconstruction processing according to this embodiment will be described with reference to FIG. 11. Note that the same reference symbols as those in FIG. 6 denote the same processes and a description thereof will be omitted.

Figure 9B:
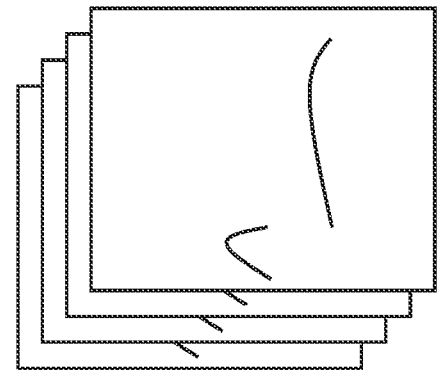
Figure 9A:
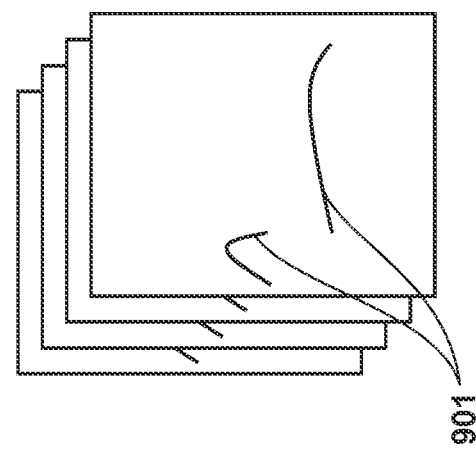

In step S1110, projection images are obtained. This processing is performed by obtaining projection images while no object 202 exists, for example, before shipping from a factory or at the time of apparatus calibration. In each of the plurality of projection images obtained by this processing, there exist fixed patterns each having an indeterminate shape as indicated by 901 in FIG. 9A. In step S1111, the reconstruction filter unit 819 performs reconstruction filter processing for each of the plurality of projection images obtained in step S1110. As a result, as shown in FIG. 9B, a plurality of projection images in each of which the fixed patterns are emphasized are obtained. In step S1112, the plurality of projection images which have been generated in step S1111 and in each of which the fixed patterns are emphasized are added to form one image. In the processes in steps S1111 and S1112, the isocenter section is reconstructed by FBP (Filtered Back Projection). Consequently, artifact patterns each having an indeterminate shape on the isocenter section are obtained, as shown in FIG. 9C.

In step S1113, the threshold processing unit 821 binarizes, by threshold processing, the artifact patterns generated in step S1112. At this time, a set threshold may be used as the $\epsilon$ value in the fixed pattern extraction processing executed by the fixed pattern extraction unit 818. In step S1114, the binarized fixed patterns generated in step S1113 are saved in a memory. As described above, in the procedure of steps S1110 to S1114, the artifact patterns on the isocenter section can be extracted and stored.

Successive approximation reconstruction can be performed according to the same procedure as in the first embodiment. That is, an iterative equation is given by:

$$g^{k+1}=g^k-C^T(Cg^k-f)-\alpha LV^2Lg^k \qquad (24)$$

In this embodiment, however, L and V are different from those in the first embodiment in accordance with the above-described processes executed by the filter processing unit 817 and fixed pattern extraction unit 818. That is, the low-pass filter processing and fixed pattern extraction processing respectively corresponding to L and V are performed by referring to the binarized artifact patterns on the isocenter section, which have been stored in the fixed pattern storage unit 822. For example, the low-pass filter processing is performed along the tangential line of the artifact, and the fixed pattern extraction processing is performed in the normal direction of the artifact. L and V have values corresponding to these processes, respectively.

By obtaining and storing in advance the artifact patterns on the isocenter section, it is possible to calculate the energy of the artifacts each having an indeterminate shape on the isocenter section in reconstruction at the time of object imaging. In the iterative process, it is possible to suppress an increase in energy and prevent the artifacts on the isocenter section from being formed on the tomographic image.

As described above, according to this embodiment, it is possible to effectively suppress the occurrence of the artifacts each having an indeterminate shape on the isocenter section. Since the isocenter section is a section on which a clearest image is obtained, it is possible to reconstruct a tomographic image with high diagnostic performance by using the above-described method, as compared with the conventional method.

According to the present invention, it is possible to effectively reduce the artifacts on the isocenter section.

Other Embodiments

Note that the present invention is not limited to the above-described embodiments, and various changes and modifications can be made without departing from the scope of the present invention. For example, the present invention can take the form of a system, an apparatus, a method, a program, a storage medium, or the like.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-243375, filed Dec. 1, 2014, which is hereby incorporated by reference herein in its entirety.

What is claimed is:

1. An image processing apparatus for reconstructing a tomographic image of a subject based on a plurality of projection images obtained by detecting, by a detection unit, radiation emitted from a plurality of different positions, comprising:
   a CPU; and
   at least one memory, the CPU and the at least one memory cooperating to provide:
      a reconstruction unit configured to reconstruct a first tomographic image from the plurality of projection images;
      an extraction unit configured to extract a fixed pattern occurring in the first tomographic image due to the detection unit;
      an update unit configured to form a second tomographic image by updating the first tomographic image using a value concerning intensity of the fixed pattern; and
      an output unit configured to output, as the tomographic image of the subject, the second tomographic image after update,
      wherein the update unit updates the first tomographic image based on differences between the projection image of the first tomographic image before update and a projection image of the second tomographic image after update.

2. The apparatus according to claim 1, wherein the update unit iterates update of a tomographic image until a difference between a tomographic image before update and a tomographic image after update becomes not larger than a predetermined value.

3. The apparatus according to claim 1, wherein the update unit iterates update of a tomographic image, and ends update when the number of update operations reaches a predetermined number.

4. The apparatus according to claim 1, wherein
   the reconstruction unit can reconstruct tomographic images with respect to sections at different heights, and
   the update unit updates the tomographic image by using, as the value concerning the intensity of the fixed pattern, a term obtained by multiplying the intensity of the fixed pattern by a coefficient determined in correspondence with a section height concerning the first tomographic image.

5. The apparatus according to claim 4, wherein
   in accordance with movement of the position from which the radiation is emitted, a position of the detection unit is moved in a direction opposite to the moving direction of the position from which the radiation is emitted, and
   the coefficient has a larger value as the section height is closer to a height of a plane including a point where a straight line connecting one point of the detection unit and a first position from which the radiation is emitted intersects a straight line connecting the one point of the detection unit and a second position from which the radiation is emitted and which is different from the first position.

6. The apparatus according to claim 1, wherein the extraction unit extracts the fixed pattern from an image obtained after low-pass filter processing is performed for the first tomographic image.

7. The apparatus according to claim 6, wherein
   the fixed pattern includes a pattern having a straight line shape, and
   the extraction unit extracts the fixed pattern from an image obtained after the low-pass filter processing is performed in a direction parallel to the pattern having the straight line shape.

8. The apparatus according to claim 7, wherein the CPU and the at least one memory further cooperate to provide an obtaining unit configured to obtain a shape of the fixed pattern from a projection image obtained while no subject is included,
   wherein based on the obtained shape, the extraction unit determines a direction in which the low-pass filter processing is performed.

9. The apparatus according to claim 6, wherein
   the fixed pattern includes a pattern having a curved line shape, and
   the extraction unit extracts the fixed pattern from an image obtained after the low-pass filter processing is performed in a tangential direction of the pattern having the curved line shape.

10. A radiation imaging system comprising:
    a CPU; and
    at least one memory, the CPU and the at least one memory cooperating to provide:
       a movable emitting unit configured to emit radiation;
       a detection unit configured to detect the radiation; and
       an image processing unit configured to reconstruct a tomographic image of a subject based on a plurality of projection images obtained by detecting, by a detection unit, the radiation emitted by the emitting unit from a plurality of different positions,
       the image processing unit further including
       a reconstruction unit configured to reconstruct a first tomographic image from the plurality of projection images,
       an extraction unit configured to extract a fixed pattern occurring in the first tomographic image due to the detection unit,
       an update unit configured to form a second tomographic image by updating the first tomographic image using a value concerning intensity of the fixed pattern, and
       an output unit configured to output, as the tomographic image of the subject, the second tomographic image after update,
       wherein the update unit updates the first tomographic image based on differences between the projection image of the first tomographic image before update and a projection image of the second tomographic image after update.

11. A control method for an image processing apparatus for reconstructing a tomographic image of a subject based on a plurality of projection images obtained by detecting, by a detection unit, radiation emitted from a plurality of different positions, the method comprising:
    reconstructing a first tomographic image from the plurality of projection images;
    extracting a fixed pattern occurring in the first tomographic image due to the detection unit;

forming a second tomographic image by updating the first tomographic image using a value concerning intensity of the fixed pattern; and outputting, as the tomographic image of the subject, the second tomographic image after update, wherein the first tomographic image is updated based on differences between the projection image of the first tomographic image before update and a projection image of the second tomographic image after update.

12. A control method for a radiation imaging system including a movable emitting unit configured to emit radiation, a detection unit configured to detect the radiation, and an image processing unit configured to reconstruct a tomographic image of a subject based on a plurality of projection images obtained by detecting, by a detection unit, the radiation emitted by the emitting unit from a plurality of different positions, the method comprising:

by the image processing unit,
reconstructing a first tomographic image from the plurality of projection images;
extracting a fixed pattern occurring in the first tomographic image due to the detection unit;
forming a second tomographic image by updating the first tomographic image using a value concerning intensity of the fixed pattern; and
outputting, as the tomographic image of the subject, the second tomographic image after update,
wherein the first tomographic image is updated based on differences between the projection image of the first tomographic image before update and a projection image of the second tomographic image after update.

13. A non-transitory computer-readable storage medium storing a computer program for causing a computer of an image processing apparatus for reconstructing a tomographic image of a subject based on a plurality of projection images obtained by detecting, by a detection unit, radiation emitted from a plurality of different positions, to:

reconstruct a first tomographic image from the plurality of projection images;
extract a fixed pattern occurring in the first tomographic image due to the detection unit;
form a second tomographic image by updating the first tomographic image using a value concerning intensity of the fixed pattern; and
output, as the tomographic image of the subject, the second tomographic image obtained after update,
wherein the first tomographic image is updated based on differences between the projection image of the first tomographic image before update and a projection image of the second tomographic image after update.

14. An image processing apparatus for reconstructing a tomographic image of a subject based on a plurality of projection images obtained by detecting, by a detection unit, radiation emitted from a plurality of different positions, comprising:

a CPU; and
at least one memory, the CPU and the at least one memory cooperating to provide:
a reconstruction unit configured to reconstruct a first tomographic image from the plurality of projection images;
an extraction unit configured to extract a fixed pattern occurring in the first tomographic image due to the detection unit;
an update unit configured to form a second tomographic image by updating the first tomographic image using a value concerning intensity of the fixed pattern; and
an output unit configured to output, as the tomographic image of the subject, the second tomographic image after update,
wherein the update unit iterates update of a tomographic image until a difference between a tomographic image before update and a tomographic image after update becomes not larger than a predetermined value related to artifacts due to the fixed pattern.

15. A control method for an image processing apparatus for reconstructing a tomographic image of a subject based on a plurality of projection images obtained by detecting, by a detection unit, radiation emitted from a plurality of different positions, the method comprising:

reconstructing a first tomographic image from the plurality of projection images;
extracting a fixed pattern occurring in the first tomographic image due to the detection unit;
forming a second tomographic image by updating the first tomographic image using a value concerning intensity of the fixed pattern; and
outputting, as the tomographic image of the subject, the second tomographic image after update,
wherein update of a tomographic image is iterated until a difference between a tomographic image before update and a tomographic image after update becomes not larger than a predetermined value related to artifacts due to the fixed pattern.

* * * * *